(12) United States Patent
Spenser et al.

(10) Patent No.: US 7,462,191 B2
(45) Date of Patent: Dec. 9, 2008

(54) DEVICE AND METHOD FOR ASSISTING IN THE IMPLANTATION OF A PROSTHETIC VALVE

(75) Inventors: Benjamin Spenser, Caesarea (IL); Netanel Benichou, Hof-Carmel (IL); Assaf Bash, Givat Ada (IL); Amit Tubishevitz, Herzeliya (IL)

(73) Assignee: Edwards Lifesciences PVT, Inc., Irvine, CA (US)

( * ) Notice: Subject to any disclaimer, the term of this patent is extended or adjusted under 35 U.S.C. 154(b) by 103 days.

(21) Appl. No.: 11/172,128

(22) Filed: Jun. 29, 2005

(65) Prior Publication Data
US 2006/0004439 A1    Jan. 5, 2006

Related U.S. Application Data

(60) Provisional application No. 60/584,903, filed on Jun. 30, 2004.

(51) Int. Cl.
*A61F 2/06* (2006.01)

(52) U.S. Cl. .............. 623/1.23; 623/1.24; 623/2.11

(58) Field of Classification Search ........... 623/1.11, 623/2.11, 900, 904, 1.23, 1.24; 600/466, 600/585; 606/191, 192, 194, 198; 604/96.01, 604/264, 915
See application file for complete search history.

(56) References Cited

U.S. PATENT DOCUMENTS

| | | | |
|---|---|---|---|
| 3,409,013 A | 11/1968 | Berry | |
| 3,587,115 A | 6/1971 | Shiley | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,470,157 A | 9/1984 | Love | |
| 4,574,803 A | 3/1986 | Storz | |

(Continued)

FOREIGN PATENT DOCUMENTS

DE    195 32 846    3/1997

(Continued)

*Primary Examiner*—William H. Matthews
*Assistant Examiner*—Suba Ganesan
(74) *Attorney, Agent, or Firm*—David L. Hauser

(57) ABSTRACT

A system for percutaneously introducing a prosthetic valve into a patient's vasculature comprises a balloon dilatation catheter, a prosthetic valve mounted coaxial to the dilatation balloon, and a pusher member comprising a longitudinally extending tubular member encompassing the shaft of the catheter. The distal end of the pusher member preferably corresponds to the proximal end of the stent component of the prosthetic valve. The pusher member provides enhanced longitudinal pushability for facilitating advancement of the prosthetic valve to a treatment site. The system is well-suited for advancing a prosthetic valve or other medical device through an introducer sheath having a relatively small inner diameter. The introducer sheath may be formed with a tapered proximal end portion for receiving the prosthetic valve and for reducing a diameter of the prosthetic valve during advancement therethrough.

21 Claims, 15 Drawing Sheets

U.S. PATENT DOCUMENTS

| | | | |
|---|---|---|---|
| 4,612,011 A | 9/1986 | Kautzky | |
| 4,655,771 A | 4/1987 | Wallsten | |
| 4,733,665 A | 3/1988 | Palmaz | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,878,495 A | 11/1989 | Grayzel | |
| 4,878,906 A | 11/1989 | Lindemann et al. | |
| 4,883,458 A | 11/1989 | Shiber | |
| 4,966,604 A | 10/1990 | Reiss | |
| 4,979,939 A | 12/1990 | Shiber | |
| 4,986,830 A | 1/1991 | Owens et al. | |
| 5,007,896 A | 4/1991 | Shiber | |
| 5,026,366 A | 6/1991 | Leckrone | |
| 5,047,041 A | 9/1991 | Samuels | |
| 5,059,177 A | 10/1991 | Towne et al. | |
| 5,085,635 A | 2/1992 | Cragg | |
| 5,089,015 A | 2/1992 | Ross | |
| 5,152,771 A | 10/1992 | Sabbaghian et al. | |
| 5,167,628 A | 12/1992 | Boyles | |
| 5,295,958 A | 3/1994 | Shturman | |
| 5,443,446 A | 8/1995 | Shturman | |
| 5,480,424 A | 1/1996 | Cox | |
| 5,749,890 A | 5/1998 | Shaknovich | |
| 5,855,597 A | 1/1999 | Jayaraman | |
| 5,925,063 A | 7/1999 | Khosravi | |
| 5,957,949 A | 9/1999 | Leonhardt et al. | |
| 6,027,525 A | 2/2000 | Suh et al. | |
| 6,171,335 B1 | 1/2001 | Wheatley et al. | |
| 6,221,091 B1 | 4/2001 | Khosravi | |
| 6,245,102 B1 | 6/2001 | Jayaraman | |
| 6,299,637 B1 | 10/2001 | Shaolia et al. | |
| 6,302,906 B1 | 10/2001 | Goicoechea et al. | |
| 6,380,457 B1 * | 4/2002 | Yurek et al. | 623/1.11 |
| 6,425,916 B1 | 7/2002 | Garrison et al. | |
| 6,440,164 B1 | 8/2002 | Di Matteo et al. | |
| 6,461,382 B1 | 10/2002 | Cao | |
| 2002/0072789 A1 * | 6/2002 | Hackett et al. | 623/1.12 |
| 2004/0093005 A1 * | 5/2004 | Durcan | 606/194 |

FOREIGN PATENT DOCUMENTS

| | | |
|---|---|---|
| DE | 195 46 692 | 6/1997 |
| DE | 198 57 887 | 7/2000 |
| DE | 199 07 646 | 8/2000 |
| DE | 10049812 | 4/2002 |
| DE | 10049813 | 4/2002 |
| DE | 10049814 | 4/2002 |
| DE | 10049815 | 4/2002 |
| EP | 0 144167 | 6/1985 |
| EP | 0 597967 | 12/1994 |
| EP | 0850607 | 7/1998 |
| EP | 1057460 | 12/2000 |
| EP | 1088529 | 4/2001 |
| EP | 1472996 | 11/2004 |
| FR | 2788217 | 12/1999 |
| GB | 2056023 | 3/1981 |
| SU | 1271508 | 11/1986 |
| WO | WO 9117720 | 11/1991 |
| WO | WO 9217118 | 10/1992 |
| WO | WO 9301768 | 2/1993 |
| WO | WO 9829057 | 7/1998 |
| WO | WO 9933414 | 7/1999 |
| WO | WO 9940964 | 8/1999 |
| WO | WO 9947075 | 9/1999 |
| WO | WO 0041652 | 7/2000 |
| WO | WO 0047139 | 8/2000 |
| WO | WO 0149213 | 7/2001 |
| WO | WO 0154625 | 8/2001 |
| WO | WO 0162189 | 8/2001 |
| WO | WO 0164137 | 9/2001 |
| WO | WO 0197715 | 12/2001 |
| WO | WO 0236048 | 5/2002 |
| WO | WO 0241789 | 5/2002 |
| WO | WO 0243620 | 6/2002 |
| WO | WO 0247575 | 6/2002 |
| WO | WO 03003949 | 1/2003 |
| WO | WO 03011195 | 2/2003 |
| WO | WO 03028592 | 4/2003 |
| WO | WO 03037227 | 5/2003 |
| WO | WO 03094793 | 11/2003 |
| WO | WO 2004058106 | 7/2004 |
| WO | WO 2004089250 | 10/2004 |
| WO | WO 2004089253 | 10/2004 |
| WO | WO 2004093728 | 11/2004 |
| WO | WO 2004105651 | 12/2004 |
| WO | WO 2005002466 | 1/2005 |
| WO | WO 2005004753 | 1/2005 |
| WO | WO 2005009285 | 2/2005 |
| WO | WO 2005011534 | 2/2005 |
| WO | WO 2005011535 | 2/2005 |
| WO | WO 2005023155 | 3/2005 |
| WO | WO 2005027790 | 3/2005 |
| WO | WO 2005046528 | 5/2005 |

\* cited by examiner

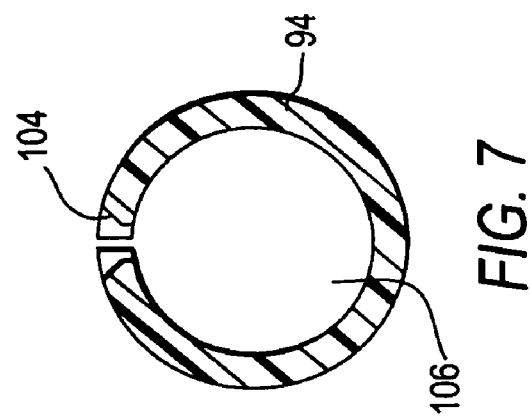
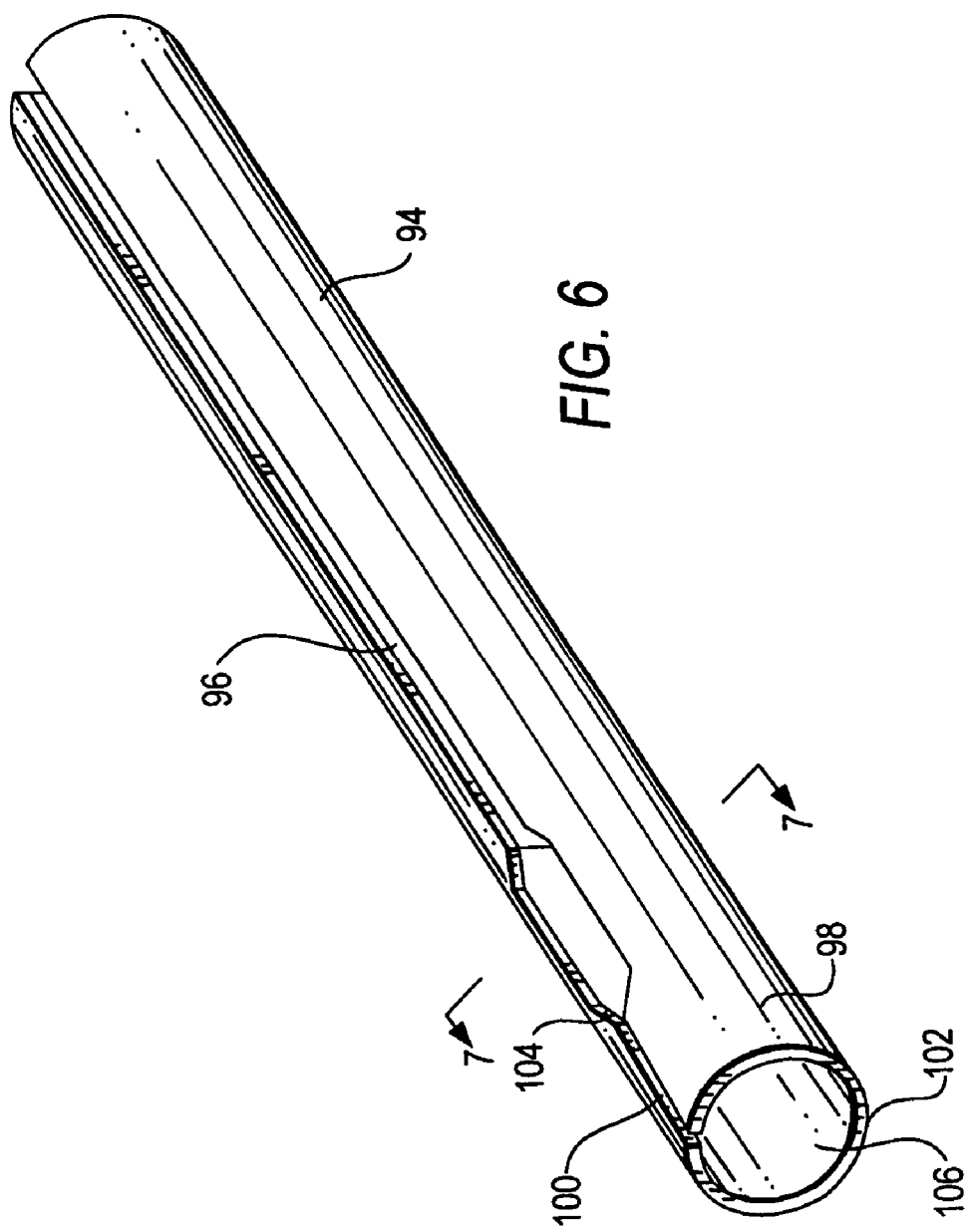

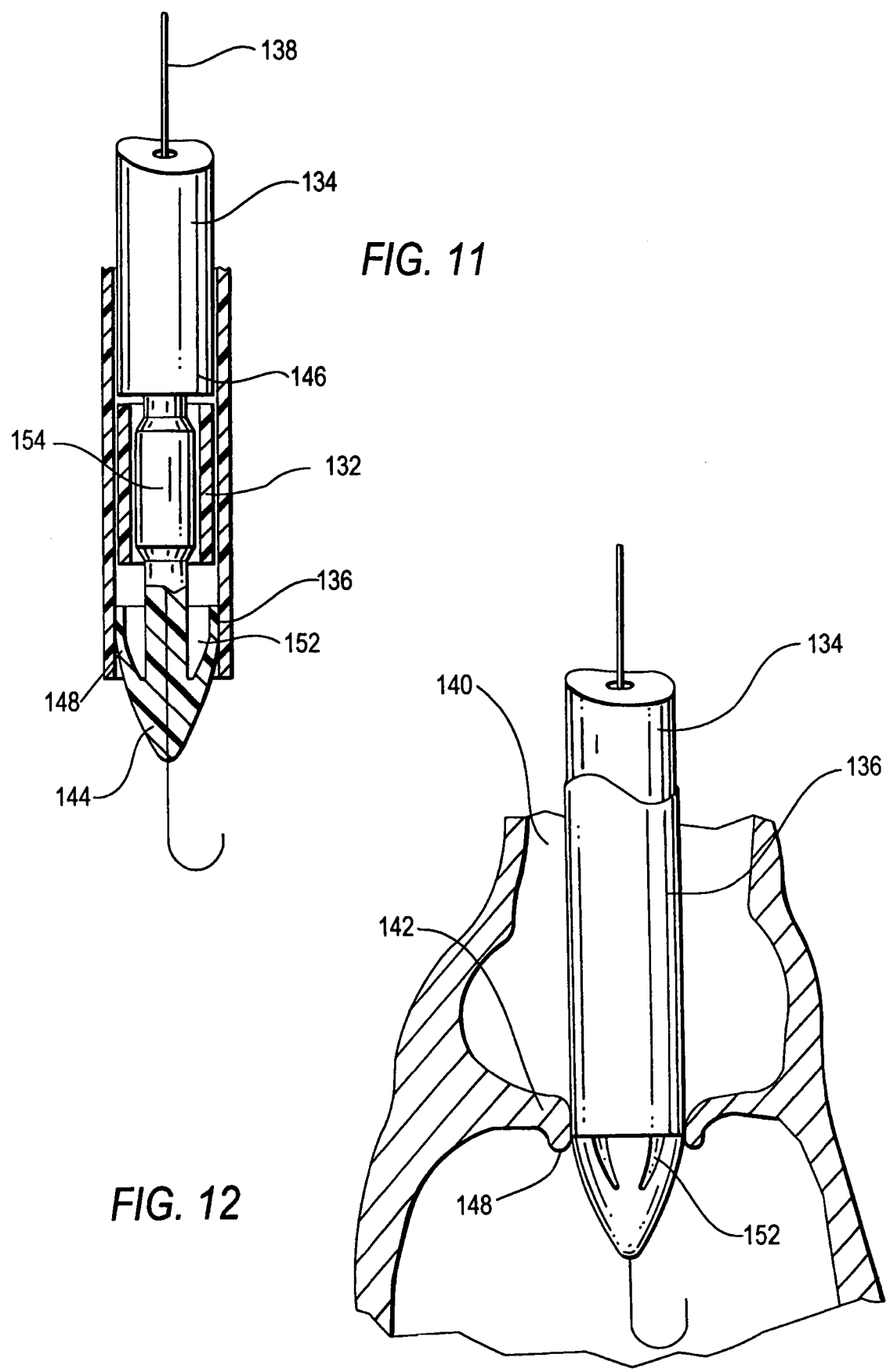

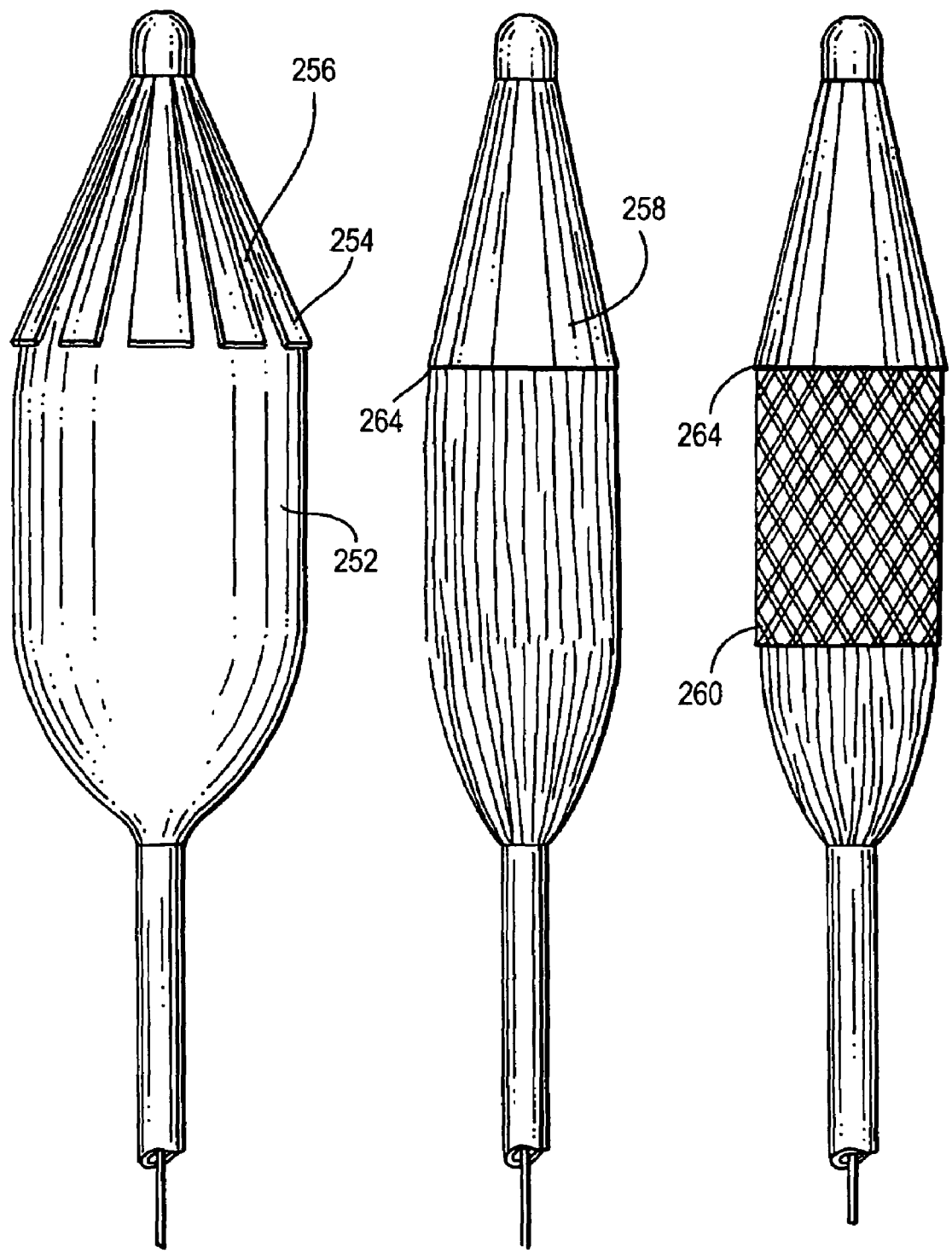
*FIG. 28*  *FIG. 29*  *FIG. 30*

DEVICE AND METHOD FOR ASSISTING IN THE IMPLANTATION OF A PROSTHETIC VALVE

RELATED APPLICATION

The present application claims priority under 35 U.S.C. §119(e) to U.S. provisional application 60/584,903, filed Jun. 30, 2004.

FIELD OF THE INVENTION

The present invention relates to methods and devices for implanting medical devices in a human body. More particularly, the present invention relates to methods and devices for assistance in implanting a prosthetic valve in a patient's heart or other body duct.

BACKGROUND OF THE INVENTION

The implantation of prosthetic valves using percutaneous techniques is a relatively new field of medicine. While percutaneous implantation has yet to achieve widespread acceptance, there are several companies developing such procedures and products. In this field, it has been found that stented valves are particularly well-suited for percutaneous advancement to a treatment site. Stented valves can be divided basically into two groups: self-expanding stented valves and expandable, i.e., internally-expanded, stented valves, which are most commonly expanded by balloons. Self-expanding stents are usually made from shape memory materials, such as nickel-titanium alloys, or Nitinol, which have a high elastic range. Balloon expandable stents are typically formed of a plastically deformable material having a high radial strength, such as such as stainless steel, platinum, iridium, cobalt-chromium, and the like.

Before delivery to a treatment site, a self-expanding stented valve may be compressed and inserted into a small tube. The stented valve is guided, i.e., pushed or pulled, distally, through the tube to a desired location and then released from the restricting tube or sheath. The stent then expands to its set diameter, or until it is restrained from further expansion by lumen walls. The expansion is caused by the stent's internal elastic radial forces. In some cases an additional force applied by, for example, a balloon, expands the stent to its final diameter.

A balloon expandable stented valve may be crimped from a large set diameter to a small crimped diameter and then moved into a patient's body ducts via an introducer sheath. After the stented valve reaches a desired position in the body, the stented valve is then expanded back to its set diameter by an external force, such as that created by an inflatable dilatation balloon.

Although stented valves may be crimped or compressed to a smaller diameter for delivery purposes, it has been found that some degree of recoil occurs after the crimping or compression process. This is a particularly undesirable feature because the stented valve is typically advanced through an introducer sheath. Furthermore, the size of the introducer sheath is limited by the size of the entry into a patient's blood vessel. Therefore, due to recoil and other factors, when the size of the entry into the patient's blood vessel is small, it can be difficult or impossible to advance the stented valve through the introducer sheath.

Accordingly, an urgent need exists for an improved system for assisting in the delivery of medical devices, such as stented prosthetic valves, into a patient's vasculature. It is desirable that such a system be particularly well-suited for use with prosthetic valves formed with self-expanding or balloon expandable stents. It is also desirable that such a system facilitates the delivery of prosthetic valves through introducer sheaths. The present invention addresses this need.

SUMMARY OF THE INVENTION

Embodiments of the present invention provide devices and methods for delivering a medical device into a patient's vasculature. Preferred embodiments facilitate percutaneous delivery of a medical device via an introducer sheath. More particularly, embodiments of the present invention provide devices and methods for facilitating advancement of a stented prosthetic valve through an introducer sheath by enhancing pushabilty and/or reducing the diameter of the crimped prosthetic valve.

In one preferred embodiment, a system for percutaneously introducing a prosthetic valve into a patient's vasculature comprises a balloon dilatation catheter having an elongate shaft and a dilatation balloon disposed along a distal end portion. A prosthetic valve is formed with an expandable stent member and a valvular structure and the prosthetic valve is positioned coaxially to the dilatation balloon. A pusher member is formed with a longitudinal slot for accepting the elongate shaft, the pusher member having a distal end corresponding to a proximal end of the expandable stent for transferring longitudinal forces to the expandable stent from a location outside the patient's vasculature, the pusher member being slidable relative to the elongate shaft. In one variation, the longitudinal slot comprises at least one area that is wider than a remaining portion of the slot. In another variation, a cover member is positioned over a distal end of the dilatation balloon, the cover member having two or more substantially equally spaced openings arranged around the cover member. The dilatation balloon may expand through the openings as the dilatation balloon is inflated. In another variation, a cover member is positioned over a distal end of the dilatation balloon, the cover member comprising a multitude of substantially equally sized members that form a substantially conical shape before the balloon is inflated. To create a seal between the pusher member and the introducer sheath, a cooperating sealing member may be provided that can be advanced distally over the pusher member. To further assist in the advancement of the prosthetic valve, the pusher member may further comprise at least one internal support member.

In another preferred embodiment, a system for assisting in introduction and implantation in a body lumen of a crimped stent-mounted percutaneous valve assembly is provided wherein the valve assembly is carried on a delivery catheter comprising a shaft and stent expansion mechanism. The system includes a pusher member comprising a slotted tube that accepts the shaft, the distal end of the pusher member being sized for contact with a proximal end of the valve assembly. An introducer sheath is formed with a tapered opening configured to provide further crimping of the assembly when the valve assembly is longitudinally advanced through the tapered opening. A tapering is provided along a distal end of the valve assembly enabling the valve assembly to avoid catching on obstructions in the lumen. To increase the contact area between the distal end of the pusher member and the proximal end of the valve assembly, the slot in the pusher member may be relatively narrow along the distal end portion. A widening region may be provided along the pusher member proximal to the narrow portion for facilitating insertion of the catheter shaft into the slot. In yet another variation, the expansion mechanism may expand in such a fashion that the expansion mechanism contacts a portion of the body lumen, thereby anchoring the expansion mechanism and preventing longitudinal movement during deployment.

In another preferred embodiment, a method of introducing a prosthetic valve into a body lumen comprises a first step of providing a balloon catheter having an elongate shaft and an expandable balloon, the prosthetic valve being disposed over the balloon. The elongate shaft is snapped into a slot formed in a pusher member, the pusher member having a distal end sized for contacting a proximal end of the prosthetic valve. An introducer sheath is inserted into the body lumen. The prosthetic valve is advanced through the introducer to a site of a native valve by applying longitudinal forces to the prosthetic valve via the pusher member. The pusher member is then withdrawn relative to the prosthetic valve and the balloon is inflated for expanding the prosthetic valve at the site of the native valve for replacing the function of the native valve.

BRIEF DESCRIPTION OF THE DRAWINGS

To better understand the present invention, and to appreciate its practical applications, the following drawings are provided and referenced hereafter. It should be noted that the drawings are given as examples only and in no way limit the scope of the invention as defined in the appended claims. Like components are denoted by like reference numerals:

FIGS. 4 and 5 are top views of the mounted valve on the introducing balloon during and after crimping wherein FIG. 4 shows the device while being crimped, and FIG. 5 shows in a dashed line the final valve outer diameter after recoil;

FIG. 6 illustrates an oblique view of a pusher member according to the invention, and FIG. 7 is a cross-sectional view along line 7-7 in FIG. 6;

FIGS. 11 and 12 illustrate a self-expandable stented valve being pushed by a pusher member through an introducer sheath;

FIGS. 28 to 30 show another a balloon-based delivery device for introducing a prosthetic valve into its desired implantation, the device having an additional portion on its tip creating a taper, improving the ability to pass through a calcific native valve.

DETAILED DESCRIPTION OF THE INVENTION

Figure 1:
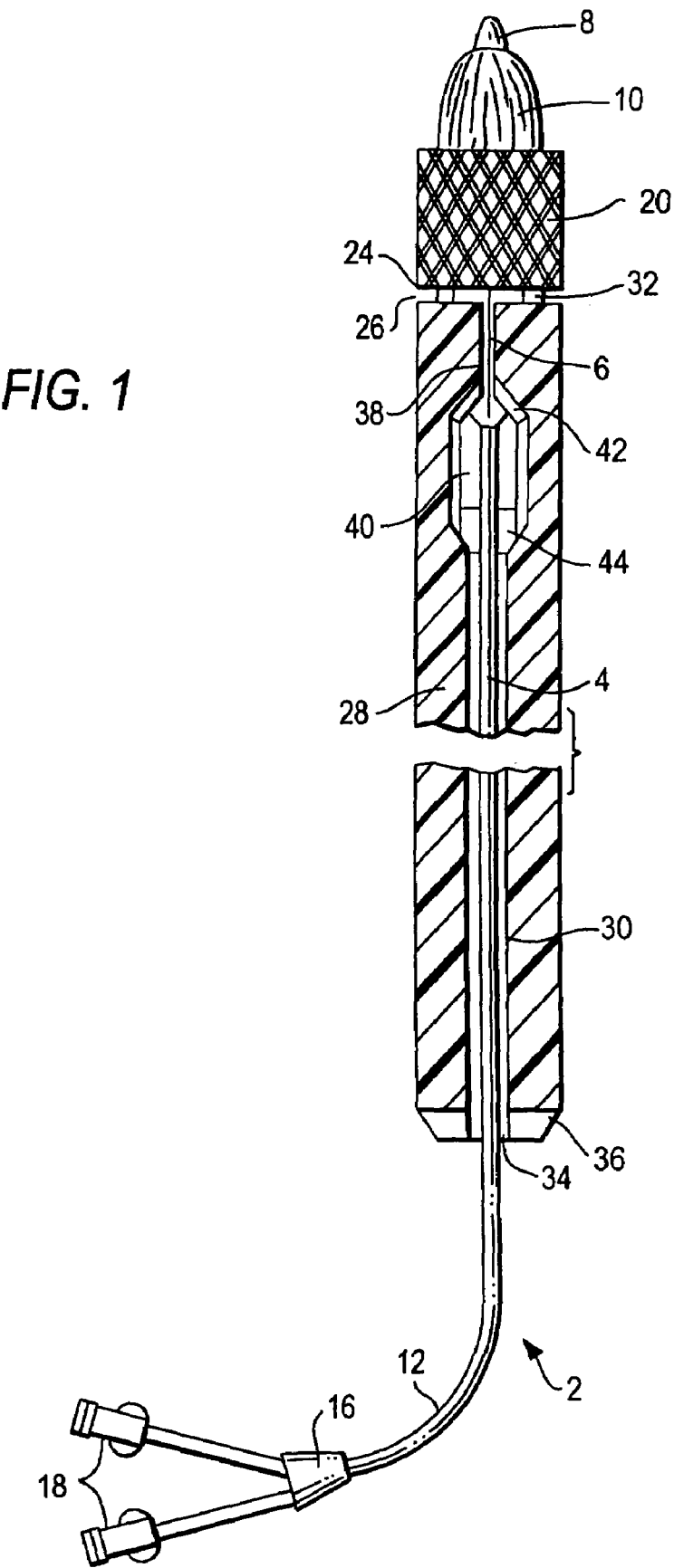
FIG. 1 illustrates a general view of a stented valve mounted on a balloon catheter, assembled with a pusher member, ready to be inserted through an introducer sheath.

Preferred embodiments of the present invention provide devices and methods for facilitating advancement of a stented prosthetic valve through an introducer sheath to a treatment site. With reference now to the partial cross-sectional view of FIG. 1, for purposes of illustration, a balloon dilatation catheter 2 is shown. The balloon dilatation catheter 2 comprises a catheter shaft 4, which extends distally through a non-inflated dilatation balloon 6. The distal portion 8 of shaft 4 extends distally of the distal end 10 of dilatation balloon 6. Catheter shaft 4 has at least one lumen (not shown) capable of slidably receiving a guidewire (not shown).

The proximal end 12 of catheter 2 comprises a junction 16 in fluid communication with one or more manifolds 18 for entry of a guidewire, for example, or another device, substance, or fluid. For example, one manifold 18 may be in fluid communication with an inflation lumen (not shown) for dilatation balloon 6, and another manifold 18 may be in fluid communication with a lumen (not shown) capable of receiving a guidewire, other device, or catheter (not shown).

A stented valve 20 is positioned coaxial and adjacent to dilatation balloon 6, where stented valve 20 is crimped onto deflated or non-inflated dilatation balloon 6. Stented valve 20 has a proximal surface 24 that is adjacent to and in contact with a distal contact surface 26 of an elongate pusher member 28. The stented valve generally comprises a substantially cylindrical stent portion which supports a valvular structure.

Delivery system shaft 4 is nested in a groove 30 in pusher member 28. The groove 30 preferably extends the entire length of pusher member 28, which is essentially a modified tube as described below and having enough stiffness to enable translation of forces applied along the linear axis of pusher member 28 to prosthetic valve 20 as described below. In various preferred embodiments, the pusher member 28 may be machined from a polypropylene rod, or a similar rigid or semi-rigid, physiologically acceptable polymer or metal.

An advantage of groove 30 is that it enables easy insertion of shaft 4 into pusher member 28 since dilatation catheter 2 has enlarged portions at each end. These enlarged portions would make it difficult or impossible to insert shaft 4 into pusher member 28 from the openings 32, 34 at the distal and proximal ends of the pusher member 28, without groove 30 providing access to them. As illustrated, the proximal end 36 of pusher member 28 is preferably tapered.

While groove 30 extends longitudinally along the length of pusher member 28, it preferably has a distal narrowing 38, to provide the largest possible contact between pusher member 28 and the contact surface 24 of prosthetic valve 20 at pushing contact area 26. A relative widening 40 of groove 30 may be provided to facilitate passing shaft 4 through narrowing 38. Widening 40 with tapered edges 42 allows the operator to more easily snap the shaft 4 through narrowing 38. Optionally pusher member 28 may have at least one support member 44.

Pusher member 28 is preferably constructed to be sufficiently pliable such that its walls can be pushed apart when shaft 4 is pushed against narrowing 38, thereby enabling insertion of shaft 4 through groove 30 into pusher member 28 even when narrowing 38 is narrower than shaft 4 itself.

Pusher member contact area 26 is the point of contact between pusher member 28 and distal end 24 of prosthetic valve 20. Pusher member 28 therefore can be used to translate force applied along the longitudinal axis of pusher member 28 directly to prosthetic valve 20. This approach differs from the traditional technique whereby a delivery system shaft 4 is alone used to push a prosthetic valve into and through an introducer sheath. Such direct pushing protects dilatation balloon 6 and minimizes or avoids the possibility of kinking of shaft 4. It will be appreciated by those skilled in the art that pusher member 28 enables the application of large longitudinal forces to a prosthetic valve or other medical device, thereby enabling passage through smaller introducer sheaths. It will also be appreciated that pusher member 28 may be used to transmit rotational forces to the prosthetic valve for maneuvering the valve into a desired alignment before or during deployment.

Figure 2:
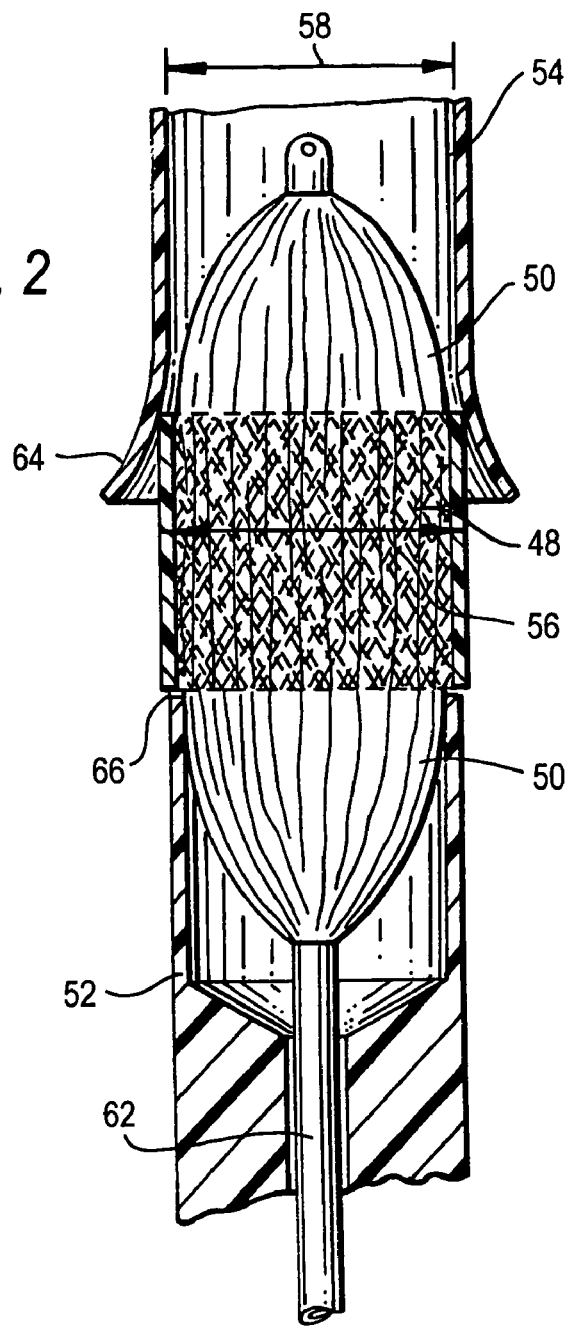

FIG. 2 illustrates an implantable prosthetic valve 48 mounted on a delivery system dilatation balloon 50 and pushed by a pusher member 52. More particularly, FIG. 2 depicts prosthetic valve 48 being pushed into an introducer sheath 54. In the illustrated embodiment, the outer diameter 56 of implantable prosthetic valve 48 is slightly larger than the inner diameter 58 of introducer sheath 54.

Figure 3:
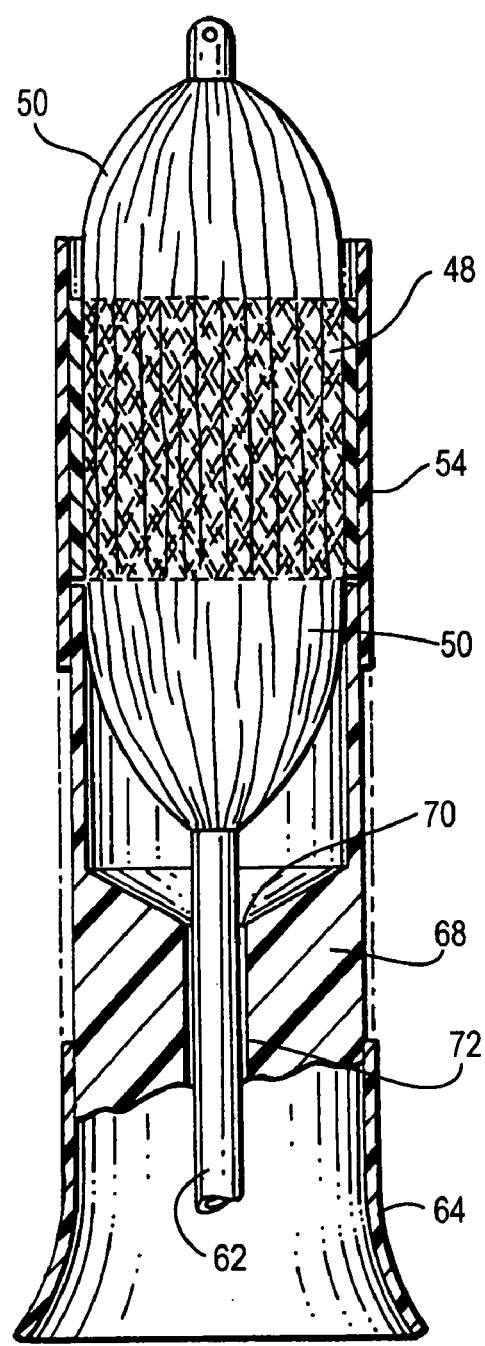
FIGS. 2 and 3 each illustrate a stented valve being pushed into an introducer sheath tube by a pusher member wherein in FIG. 2 the diameter of the valve is larger than the tube's diameter and in FIG. 3 the diameter of the valve has been reduced by advancing the valve into the sheath with the pusher member.

With reference to the partial cross-sectional drawings shown in FIGS. 2 and 3, the delivery system comprising a balloon dilation catheter shaft 62, a dilatation balloon 50, a prosthetic valve 48, and a pusher member 52 is advanced into the introducer sheath 54. The proximal end 64 of introducer sheath 54 is slightly flared. The taper in the proximal end 64 of introducer sheath 54, together with the direct pushing force applied by pusher member 52 to prosthetic valve 48 at pusher member contact area 66, enable reduction of valve outer diameter 56 to a size similar to that of sheath 54 inner diameter 58. FIG. 3 illustrates prosthetic valve 48 after having been advanced into introducer sheath 54 wherein the diameter 56 of prosthetic valve 48 has been reduced due to application of force by pusher member 52 and the geometry of taper 64.

Optionally pusher member 52 may have at least one internal support 68. Each such support 68 will have a passageway 70 for catheter shaft 62 that comprises an opening 72 commensurate with the groove or slot (not shown here). Thus, each support may have a semi-annular shape that provides additional support to pusher member 52 and/or to catheter shaft 62.

Figure 4:
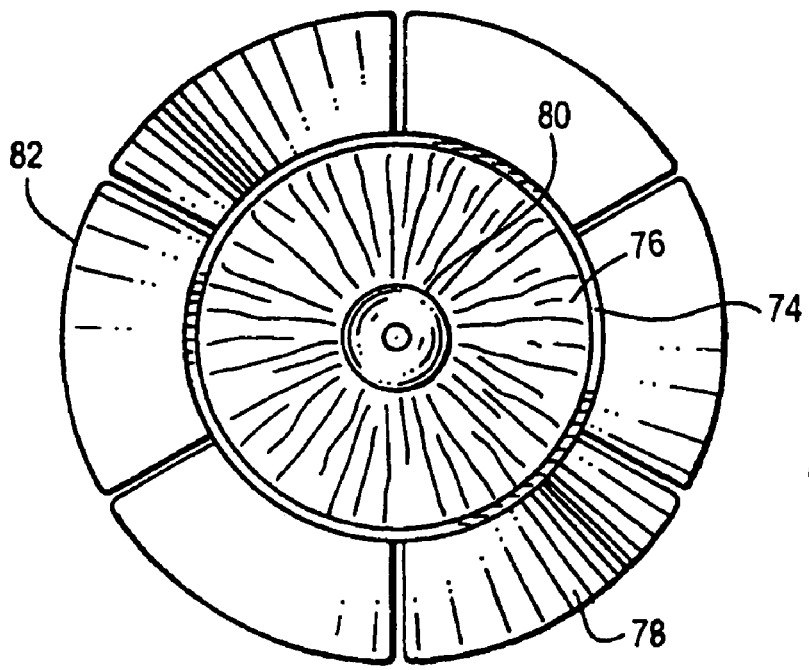
Figure 5:
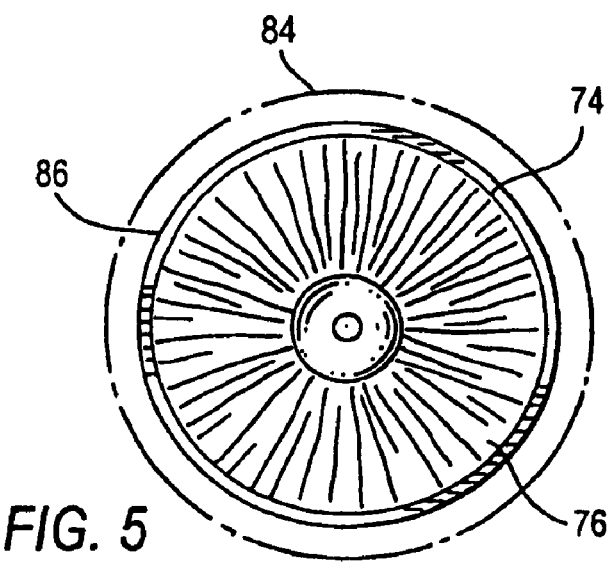

A limiting factor when a prosthetic valve is inserted is the fact that, after crimping, the valve diameter increases from its smallest possible diameter due to recoil. This effect can be seen with reference to FIGS. 4 and 5, wherein a top view is shown of a prosthetic valve 74 assembled on a folded or non-inflated balloon 76. In FIG. 4, the jaws 78 compress the prosthetic valve assembly to its smallest diameter. Balloon 76 has a central lumen 80, which may receive a guidewire 82. FIG. 5 shows the device assembly after it is released from the crimping device. With the crimping force released, the assembly recoils (expands) slightly until reaching its post-recoil circumference as shown by dotted line 84. When the prosthetic valve assembly is pushed by pusher member 28 (as shown in FIG. 2) against taper 28, the circumference of the assembly is advantageously reduced from the post-recoil circumference 84 to a reduced circumference 86.

FIGS. 6 and 7 are perspective and cross-sectional views, respectively, of one preferred embodiment of a pusher member 94. Pusher member 94 has a groove 96 along its entire length. Near the distal end 98 of pusher member 94, the groove 96 has a narrow portion 100, maximizing the pushing contact area 102. The groove 96 is preferably tapered on its edges and widened at point 104 to provide means for sliding the delivery system shaft into the groove 96. Distal end bore 106 of pusher member 94 is the receptacle for the delivery system's balloon (not shown).

Figure 8:
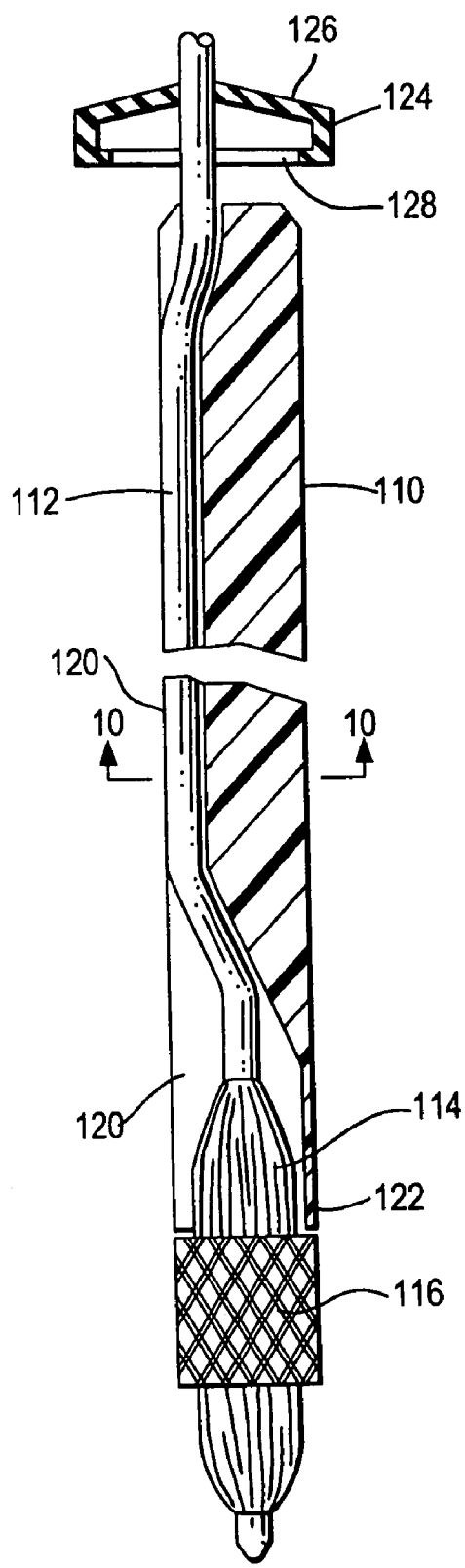
FIGS. 8 and 9 each illustrate a cross-sectional view of an assembled device including a shaft bushing.

FIG. 8 provides a cross-sectional view along the length of pusher member 110. The mounted delivery system comprises catheter shaft 112, balloon 114, and prosthetic valve 116. Groove 120 is cut along the entire length. The depth of the groove changes according to different functions along the pusher member. At the pusher member distal end 122, prosthetic valve 116 is preferably concentric to pusher member 110 so it can be pushed symmetrically through the introducer sheath. Accordingly, in the illustrated embodiment, the depth of groove 120 changes along the length of pusher member.

Figure 9:
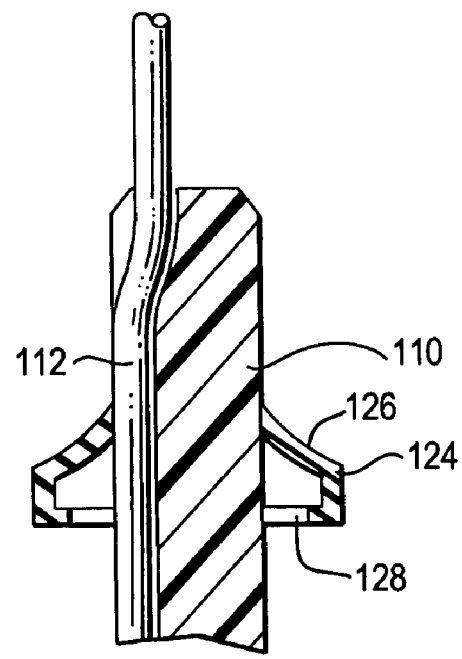

The delivery system and pusher member 110 are inserted through a standard introducer sheath (not shown) and are preferably sealed, in this case with bushing 124, which has a flexible proximal surface 126 and a distal opening 128. Therefore, the depth of groove 120 and delivery system shaft 112 create a complete sealing boundary, as seen in FIG. 9, optionally over the proximal end of an introducer sheath (not shown). Bushing 124 is made of a stretchable material, preferably a biologically compatible polymer, which can seal the shaft and can also seal the entire pusher member, as shown in FIG. 9. A taper 130 is added to the pusher member to facilitate moving the sealing bushing 124 onto the pusher member 110.

Figure 10:
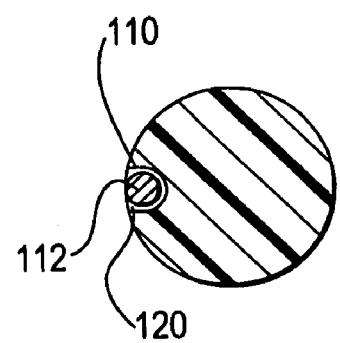
FIG. 10 is a cross-sectional view along the line 10-10 in FIG. 8.

FIG. 10 represents a cross-section of FIG. 8 across line 10-10, where catheter shaft 112 resides within groove 120 of pusher member 110.

FIG. 11 is a partial cross-sectional view of an alternative configuration wherein a self-expandable stented prosthetic valve 132 is pushed by a pusher member 134 through an introducer sheath 136 over a guidewire 138. In this case, introducer sheath 136 is guided through a patient's aorta 140 to a stenotic aortic valve 142, as shown in FIG. 12. After advancement to the desired location, prosthetic valve 132 pushed out of introducer sheath 136. Alternatively, the valve may be released by withdrawing introducer sheath 136 relative to the prosthetic valve 132.

To facilitate advancement through stenotic valve 142 with sheath 136, a tapered distal tip 144 may be formed or attached to the distal portion 146 of pusher member 134. Before introducer sheath 136 is passed through the stenotic aortic valve 142, tapered tip 144 tip is first passed through introducer sheath 132. Tapered tip 144 is preferably formed with flexible walls 148 and notches 152 that allow it to pass through sheath 136 and, when released out of sheath 136, to expand to the outer diameter of sheath 136. In that way a smooth transition is created between sheath 136 and tapered tip 144, allowing a smooth passage into the left ventricle. Valve mount 154 is proximally adjacent to tapered tip 144 and can carry the self-expanding prosthetic valve payload. Alternatively, valve mount 154 can be replaced by an assembly of an inflatable balloon (not shown) surrounded by a stented valve, with the balloon later inflated to expand the valve to its final set diameter.

Figure 13:
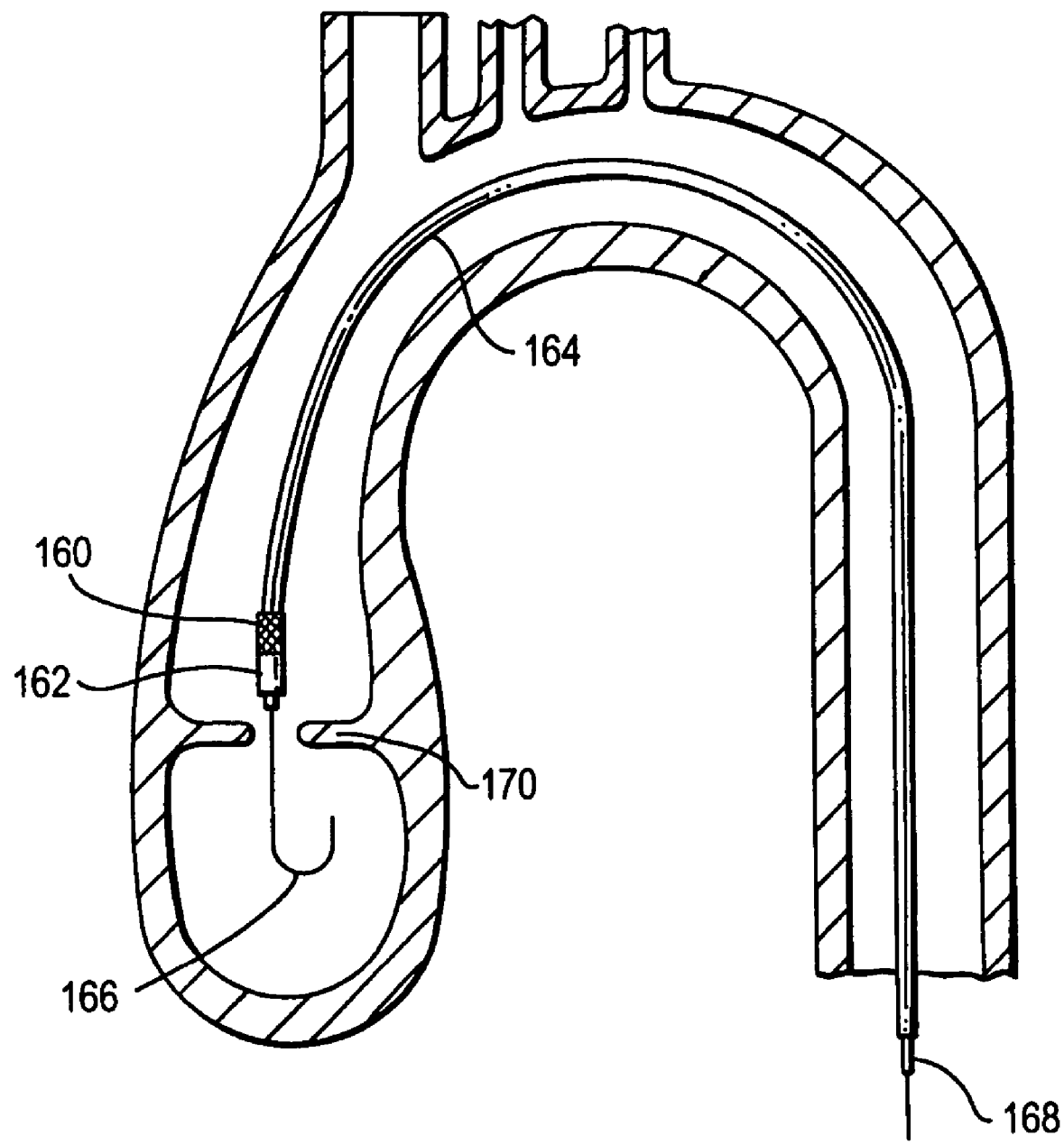
FIG. 13 illustrates a long pusher member assisting in introducing a prosthetic valve past a diseased valve and into its desired implantation location.

In FIG. 13, a preferred implantation process of a stented valve 160 mounted on an inflation balloon 162, which is part of a delivery system, is illustrated. In one advantageous feature, a bendable (i.e., flexible) pusher member 164 pushes directly on the stented valve 160. Although pusher member is bendable, pusher member is substantially rigid along its longitudinal axis for transmitting longitudinal forces to the stented valve. The absence of the pusher member would require pushing the stented valve over a guidewire 166 via the catheter shaft 168. The shaft has much less rigidity and pushing force than the pusher and in many cases would become twisted, and in some cases kinked, disabling the delivery of the valve to the desired location. In stenotic valves, the case is even worse since passing a stenotic valve 170 to place the prosthetic valve is very difficult and requires significant pushing forces. The pusher member described here enables one to achieve effective pushing forces all the way to the stenotic valve and across it.

Figure 14:
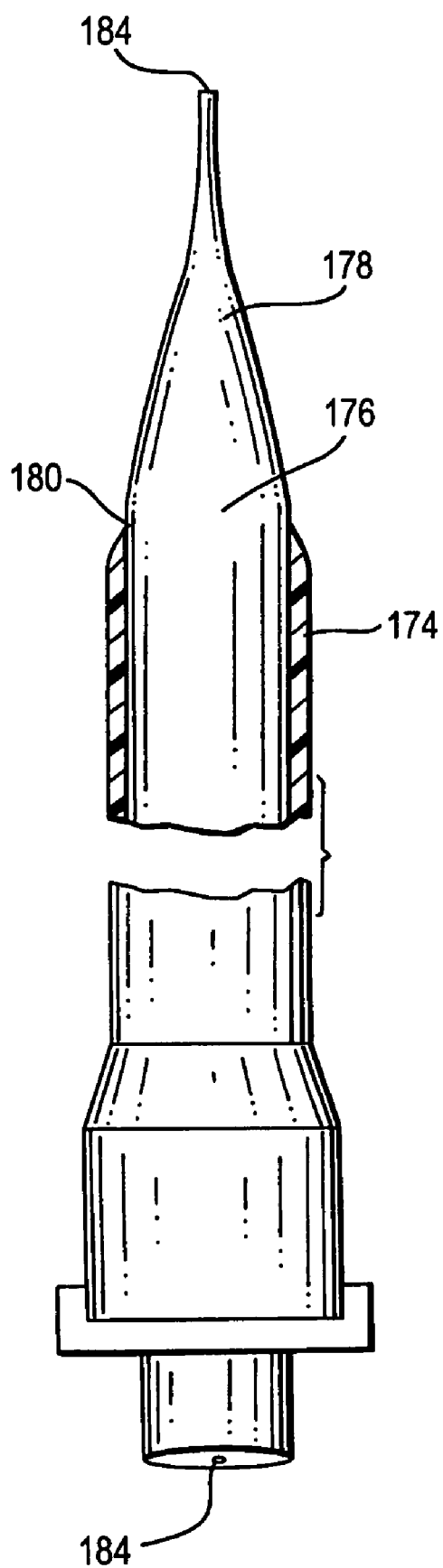
FIGS. 14 to 23 illustrate the steps according to one preferred method for inserting a prosthetic valve into a native diseased valve through a long introducer sheath.

With reference to FIGS. 14 to 23, preferred methods of using the delivery system will now be described in more detail. With reference to FIG. 14, one preferred method of use generally comprises insertion of a guiding sheath into a native calcified valve followed by implantation of a prosthetic percutaneous valve. An introducer sheath 174 is a flexible tube that can be made of various materials and could include a braided layer and have a PTFE layer in its outer and inner surfaces. The PTFE layer can be replaced with a hydrophilic or lubricious material. The purpose of sheath 174 is to provide a pathway from entry through a patient's femoral artery to the patient's aortic valve. To optimally achieve that purpose sheath 174 should be flexible enough to take the aortic arc curve and possibly torturous blood vessels. It should also have a minimal friction coefficient, as reflected by the materials and coatings indicated. A dilator 176 is inserted through introducer sheath 174. Dilator 176 has a tapered distal tip 178 that facilitates passage through a calcified aortic valve. Passing the calcified aortic valve could be difficult, and a tapered tip with no shoulders is required to pass it in an optimal way. A transition point 180 between dilator 176 and introducer sheath 174 is smooth. Dilator distal tip 178 has a lumen 184 suitable for a guidewire.

Figure 15:
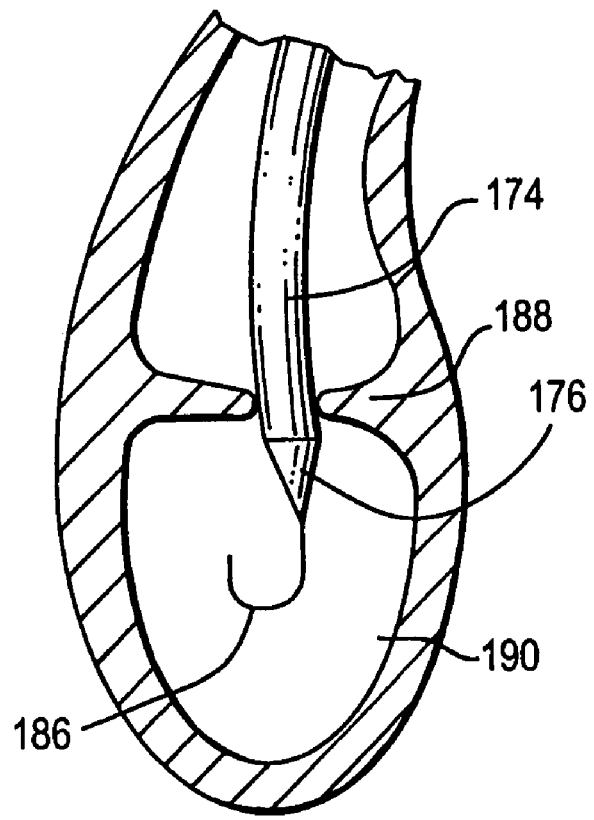
Figure 16:
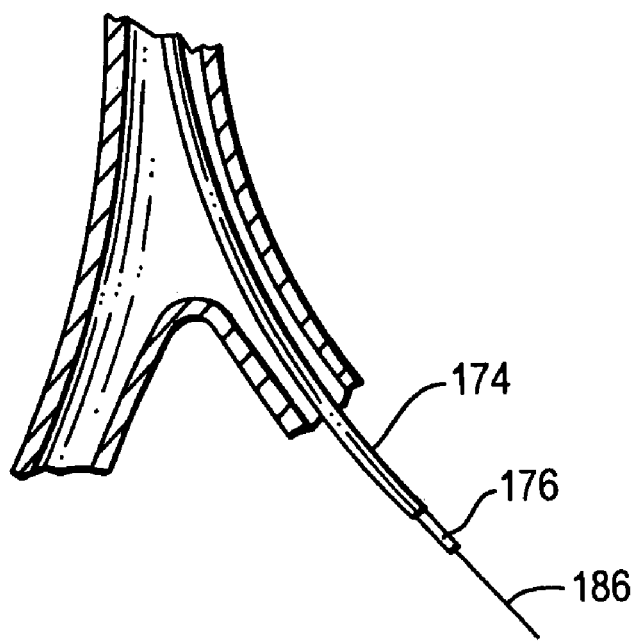

In FIG. 15, sheath 174 with dilator 178 comprising a guidewire 186 is shown positioned through a calcified aortic valve 188 into a patient's left ventricle 190. In FIG. 16, the proximal portion of sheath 174 is shown with the proximal portions of dilator 176 and guidewire 186.

Figure 17:
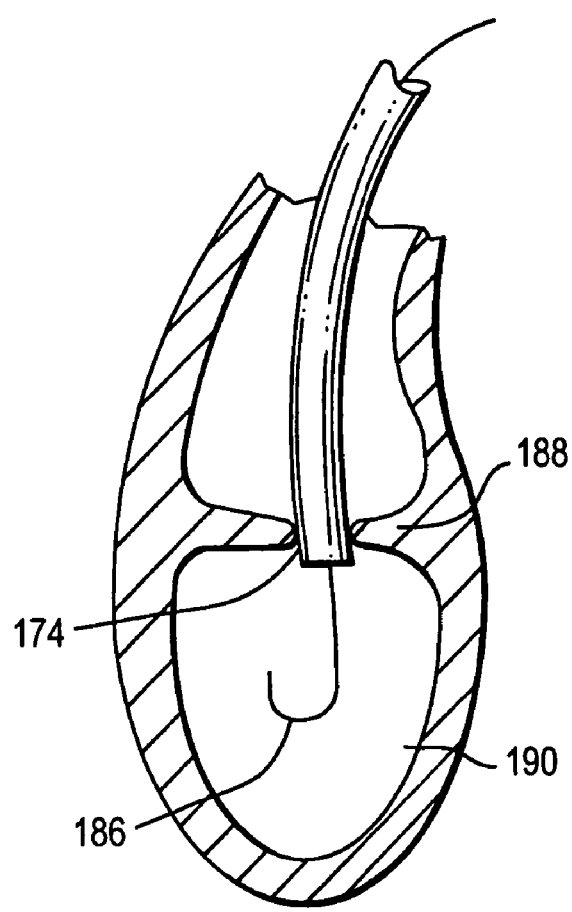
Figure 18:
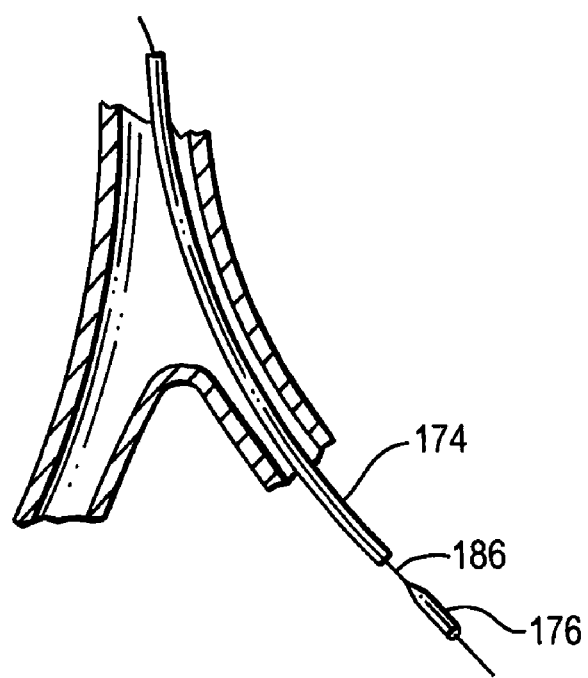
Figure 19:
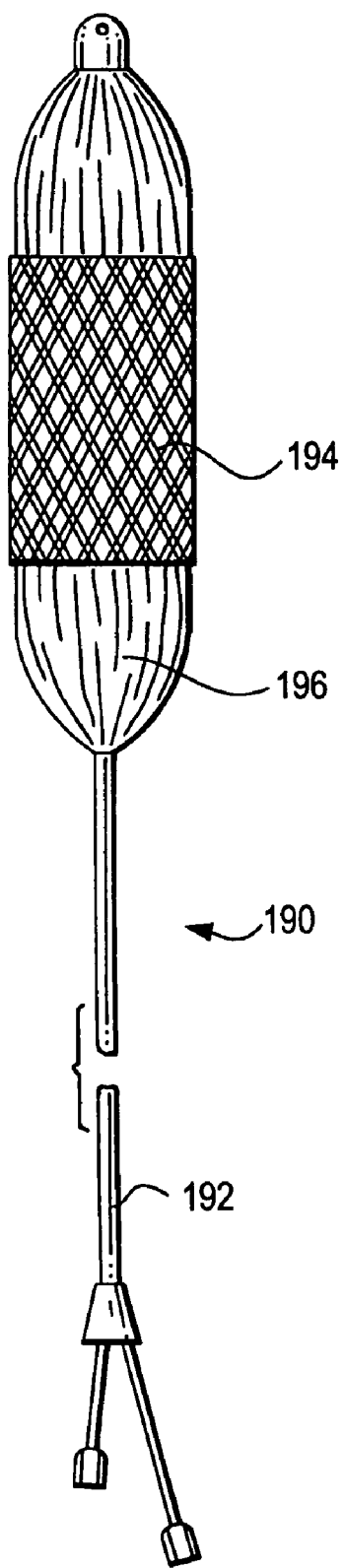
Figure 20:
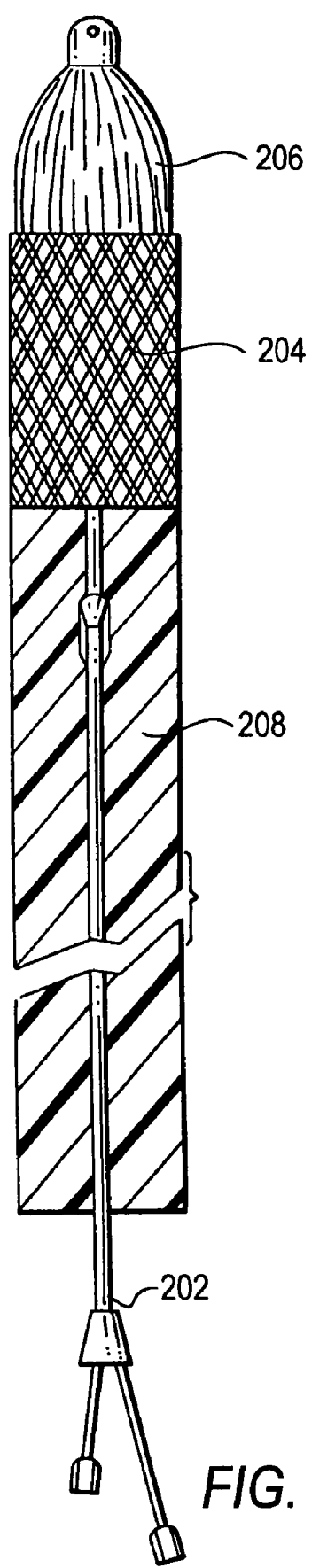

As shown in FIGS. 17 and 18, dilator 176 is withdrawn from introducer sheath 174 over guidewire 186. The distal end of sheath 174 preferably remains slightly distal to calcified aortic valve 188. A prosthetic valve may then be inserted through the introducer sheath to the implant site. FIG. 19 shows a delivery system 190 with a pushable shaft 192, prosthetic valve 194, and dilatation balloon 196. With reference now to FIG. 20, a delivery system in accordance with a preferred embodiment of the present invention, similar to the devices described above, especially in FIG. 1, generally comprises a catheter shaft 202, a prosthetic valve 204, a dilatation balloon 206, and a pusher member 208. Both of these delivery devices will push the valve through the tube to the desired location.

Figure 21:
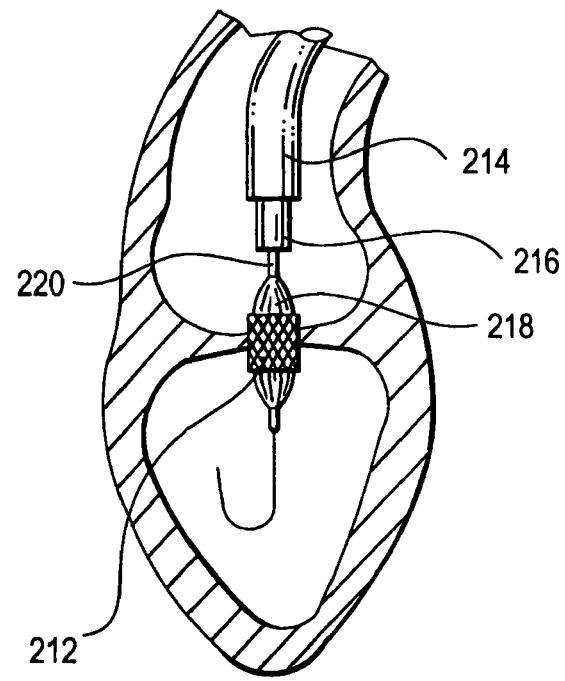
Figure 22:
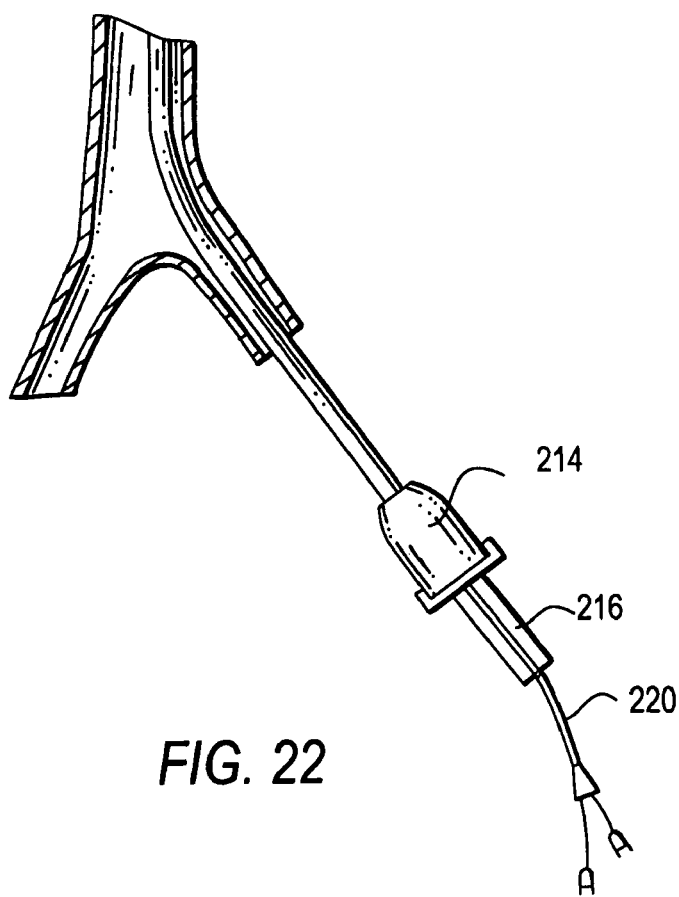
Figure 23:
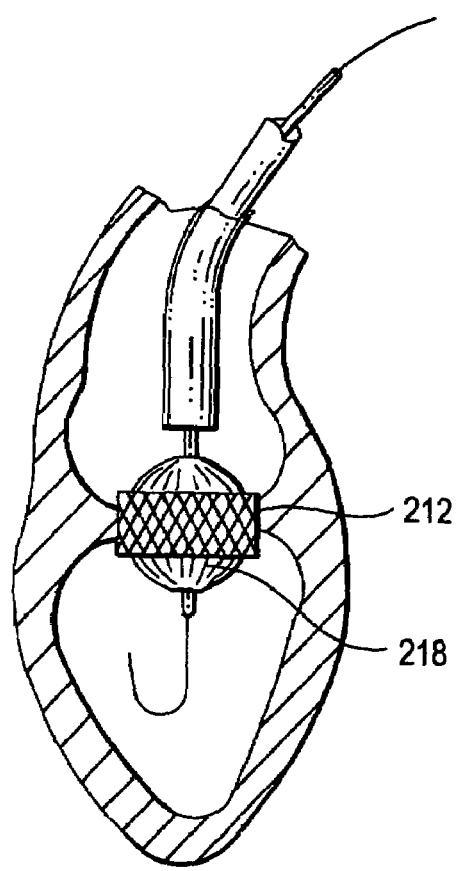

The delivery system with the valve is pushed through the tubular sheath until it emerges from the distal end, opposite the native valve leaflets. FIG. 21 shows the exposure of a prosthetic valve 212. The sheath 214 is pulled back, while the pusher member 216, balloon 218, and catheter shaft 220 are held in place. Then, pusher member 216 is pulled back while the delivery system is held in place. The crimped valve is now opposite the native leaflets ready for inflation. The distal ends of sheath 214, pusher member 216, and catheter shaft 220 are shown in FIG. 22. FIG. 23 shows the last stage of inflating balloon 218 and expanding prosthetic valve 212.

Figure 24:
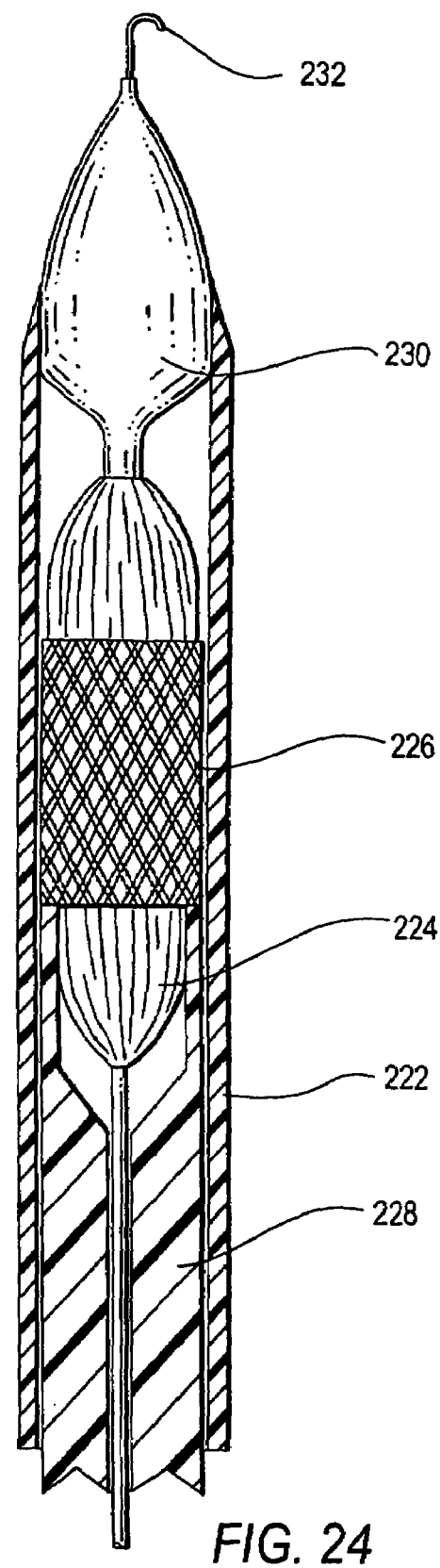
FIG. 24 shows a detail of a valve assembly on a balloon with a tapered end, which will assist in passing a calcified native valve.

With reference now to FIG. 24, a valve delivery system is inserted into a tubular introducer sheath 222, the delivery system comprising an inflatable balloon 224, a crimped valve 226, a pusher member 228, and a guiding tip 230. Guiding tip 230 has a tapered shape enabling safe passage of sheath 222 through a patient's calcified valve (not shown). It is desirable to have a tapered shape with no shoulders or irregular contours that might get caught on the calcified valve, preventing passage of tube 222. The delivery system shown in FIG. 24 is inserted over a guidewire 232. In this embodiment of the present invention, the delivery system is pushed by pusher member 228 in a fashion similar to devices shown in the drawings described above.

Figures 25, 26, 27:
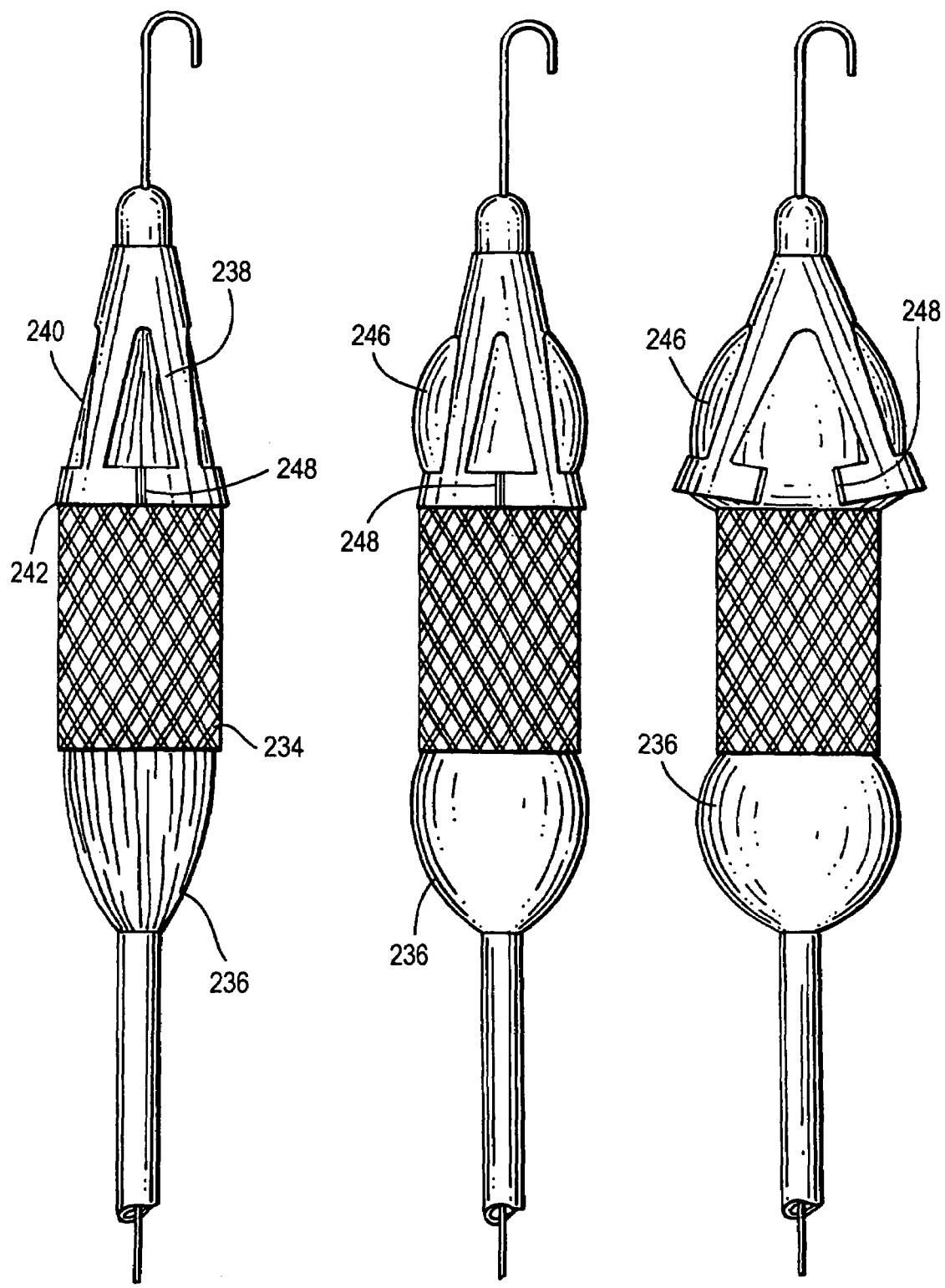
FIGS. 25 to 27 show a balloon-based delivery device for introducing a prosthetic valve into its desired implantation location, the device having an additional portion on its tip creating a taper, improving the ability to pass through a calcified native valve.

With reference to FIGS. 25 to 27, yet another embodiment of a balloon-based delivery device for introducing a prosthetic valve into its desired implantation location is shown. A stented prosthetic valve 234 is coaxially mounted on an inflatable balloon 236 covered by a tapered sleeve 238, preferably having "windows" or openings 240. This sleeve creates a continuous tapered shape, eliminating the effect of a shoulder, which normally disturbs the delivery device when trying to pass through a calcified aortic valve (not shown). Sleeve 238 either extends to the same (or a greater) diameter as (than) valve 234 at point 242. Sleeve 238 can be made of a thin flexible material that creates a tapered shape when crimped.

When balloon 236 is inflated, as shown in FIG. 26, portions 246 of balloon 236 protrude through windows 240 to create a dog-bone shape, which shape prevents prosthetic valve 234 from shifting on the balloon during inflation. As balloon 236 continues to inflate, at least one weakened area 248 on tapered sleeve 238 tears, allowing sleeve 238 to open and allowing balloon 236 to inflate to its full, final diameter. Although a preferred embodiment of a tapered sleeve is described for purposes of illustration, any suitable cover member configuration may be employed. Furthermore, a tapered sleeve similar to tapered sleeve 238 (or other cover member) could be provided on the proximal portion of balloon 236, either in addition to or instead of tapered sleeve 238.

With reference to FIGS. 28 to 30, yet another embodiment of a balloon-based delivery device is shown. FIG. 28 illustrates an inflated inflatable balloon 252 having a plurality of flaps 254 attached to the distal portion 256 of balloon 252 and arranged in a "ten-like" fashion. Flaps 254 are sized to come together when balloon 252 is deflated (FIG. 29), to form a tapered shape 258 having a proximal inner diameter corresponding to the outer diameter of a prosthetic valve 260. Prosthetic valve 260 is shown mounted on balloon 252 in FIG. 30. The proximal ends 264 of flaps 254 are crimped to a tapered shape, creating a continuous area between the taper and the prosthetic valve that will pass easily through a calcified aortic valve. The proximal end of the assembly between the stent and balloon creates a shoulder which in this case does not interfere in the insertion of the valve to the aortic native valve. However, the distal end would have had the same shoulder in the absence of flaps 254.

The materials and dimensions for the embodiments of the invention described herein are either known to or would be readily apparent to those skilled in the art. More specifically, balloon dilatation catheters and guidewires useful according to the invention are readily available commercially from suppliers such as Cook, Johnson & Johnson, Boston Scientific, and the like. Prosthetic valves are described in the literature, including U.S. patents. See, for example, U.S. Pat. Nos. 3,755,823, 4,056,854, 4,106,129, 4,222,126, 4,297,749, 4,343,048, 4,580,568, 4,777,951, 5,032,128, 5,037,434, 5,411,552, 5,840,081, 5,855,601, 5,855,602, and 6,171,335, all of which are incorporated herein by reference. Other members described herein can be fabricated from physiologically acceptable materials such as known polymers such as polypropylene, polyethylene, copolymers thereof, PTFE, and the like. The dimensions of the longitudinal members described herein will preferably range from about 100 to about 300 cm in length and from about 8 to about 20 mm in diameter.

The preceding specific embodiments are illustrative of the practice of the invention. It is to be understood, however, that other expedients known to those skilled in the art or disclosed herein, may be employed without departing from the spirit of the invention or the scope of the appended claims.

The invention claimed is:

1. A system for percutaneously introducing a prosthetic valve into a patient's vasculature, comprising:
   a balloon dilatation catheter having in elongate shaft and a dilatation balloon disposed along a distal end portion, wherein the elongate shaft comprises a width;
   a prosthetic valve formed with an expandable stent member and a valvular structure, the prosthetic valve being positioned coaxially to the dilatation balloon; and
   a pusher member having a fixed axial length and formed with a longitudinal slot extending along the entire axial length for accepting the elongate shaft, the pusher member having a distal end configured to contact a proximal end of the expandable stent member for transferring longitudinal forces to the expandable stent member from a location outside the patient's vasculature, the pusher member being slidable relative to the elongate shaft,
   wherein the pusher member comprises at least one wall extending along the entire axial length of the pusher member,
   wherein the wall of the pusher member defines a longitudinal gap in the wall, the longitudinal gap extending along the entire axial length of the pusher member and providing access to the longitudinal slot along the entire length of the longitudinal slot,
   wherein at least a portion of the longitudinal gap in the wall of said pusher member has a width that is less than the width of the elongate shaft, and
   wherein the pusher member is sufficiently pliable such that the elongate shaft can be inserted into the longitudinal slot by inserting at least a portion of the elongate shaft through the portion of the longitudinal gap that has a width less than the width of the elongate shaft.

2. The system of claim 1, wherein the longitudinal gap comprises at least one area that is wider than a remaining portion of the gap.

3. The system of claim 2, wherein the at least one area of the longitudinal gap that is wider than a remaining portion of the gap is wider than the width of the elongate shaft.

4. The system of claim 1, further comprising a cover member positioned over a distal end of the dilatation balloon, the cover member having two or more substantially equally spaced openings arranged around the cover member.

5. The system of claim 4, wherein the dilatation balloon expands through the openings as the dilatation balloon is inflated.

6. The system of claim 1, further comprising a cover member positioned over a distal end of the dilation balloon, the cover member comprises a multitude of substantially equally sized members that form a substantially conical shape before the balloon is inflated.

7. The system of claim 6, wherein each one of the multitude of substantially equally sized members are attached to the distal end of the dilation balloon.

8. The system of claim 1, further comprising a cooperating seating member that can be advanced distally over the pusher member.

9. The system of claim 1, wherein the pusher member further comprises at least one internal support member.

10. The system of claim 1, wherein the at least a portion of the longitudinal gap having a width that is less than the width of the elongate shaft is located proximate to the distal end of the pusher member.

11. The system of claim 1, wherein the longitudinal gap comprises a first portion having a first width, a second portion having a second width, and a third portion having a third width,
   wherein the third portion is located proximate to the distal end of the pusher member,
   wherein the second portion is located closer to the proximal end of the pusher member than the third portion,
   wherein the first portion is located closer to the proximal end of the pusher member than the second portion,
   wherein the third width is less than both the first width and the second width, and
   wherein the second width is greater than both the first width and second width.

12. The system of claim 11, wherein the third width is less than the width of the elongate shaft, and wherein the second width is greater than the width of the elongate shaft.

13. The system of claim 11, wherein the longitudinal slot comprises a tapered portion between the second portion and the third portion of the longitudinal gap, and wherein the tapered portion provides a gradual transition between the second width and the third width.

14. The system of claim 1, wherein the distal end of the pusher member comprises a bore for receiving the proximal end of the dilation balloon.

15. A system for assisting in introduction and implantation in a body lumen of a crimped stent-mounted percutaneous valve assembly, the valve assembly carried on a delivery catheter comprising a shaft and stent expansion mechanism, the shaft having a diameter, the system comprising:
   a pusher member comprising a longitudinally slotted tube that accepts and encompasses the shaft, the distal end of the pusher member being sized for contact with a proximal end of the valve assembly, wherein the longitudinally slotted tube comprises a longitudinal slot extending along the entire axial length of the tube, wherein the pusher member comprises at least one wall extending along the entire axial length of the pusher member, wherein the wall of the pusher member defines a longitudinal gap in the wall, the longitudinal gap extending along the entire axial length of the pusher member and providing access to the longitudinal slot along the entire length of the longitudinal slot, wherein at least a portion of the longitudinal gap in the wall has a width that is less than the diameter of the shaft, and wherein the pusher member is sufficiently pliable such that the elongate shaft can be inserted into the longitudinal slot by inserting at least a portion of the shaft through the portion of the longitudinal gap that has a width less than the diameter of the shaft;
   an introducer sheath formed with a tapered opening configured to provide further crimping of the assembly when the valve assembly is longitudinally advanced through the tapered opening; and
   a tapering distal to the valve assembly for enabling the valve assembly to avoid catching on obstructions in the lumen, the tapering having a distal tip formed with a guidewire lumen.

16. The system of claim 15, wherein the gap in the pusher member comprises at least one area that is wider than a remaining portion of the gap.

17. The system of claim 15, further comprising a cooperating sealing member that can be advanced distally over the pusher member.

18. The system of claim 15, wherein the pusher member further comprises at least one internal support member.

19. The system of claim 15, wherein the expansion mechanism expands in such a fashion that the expansion mechanism contacts a portion of the body lumen, thereby anchoring the expansion mechanism and preventing longitudinal movement during deployment.

20. A method of introducing a prosthetic valve into a body lumen, comprising:
providing a balloon catheter having an elongate shaft and an expandable balloon, the prosthetic valve being disposed over the balloon, and the elongate shaft comprising a diameter;
snapping the elongate shaft into a longitudinal slot formed in a pusher member, the slot extending along an entire length of the pusher member, the pusher member being configured to encompass the elongate shaft and having a distal end sized for contacting a proximal end of the prosthetic valve, wherein the pusher member comprises at least one wall extending along the entire axial length of the pusher member, wherein the wall of the pusher member defines a longitudinal gap in the wall, the longitudinal gap extending along the entire axial length of the pusher member and providing access to the longitudinal slot along the entire length of the longitudinal slot, and wherein snapping the elongate shaft into the longitudinal gap comprises snapping a portion of the elongate shaft through at least a portion of the longitudinal gap that has a width less than the diameter of the elongate shaft;
inserting an introducer sheath into the body lumen;
inserting the prosthetic valve into a proximal end of the introducer sheath;
advancing the prosthetic valve through the introducer sheath to a site of a native valve by applying longitudinal forces to the prosthetic valve via the pusher member;
withdrawing the pusher member relative to the prosthetic valve; and
inflating the balloon for expanding the prosthetic valve at the site of the native valve for replacing the function of the native valve.

21. The method of claim 20,
wherein snapping a portion of the elongate shaft through at least a portion of the longitudinal gap that has a width less than the diameter of the elongate shaft comprises:
positioning at least a portion of the elongate shaft adjacent to the longitudinal gap in the wall of the pusher member; and
pushing the portion of the elongate shaft through the longitudinal gap in the wall of the pusher member.

* * * * *